Figure 1:
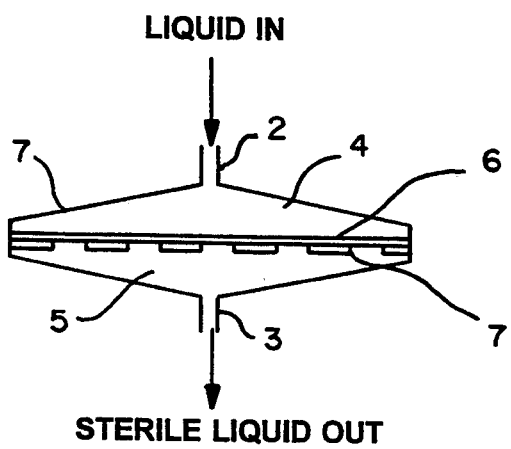

United States Patent [19]

Davis et al.

[11] Patent Number: 5,389,373
[45] Date of Patent: Feb. 14, 1995

[54] PREPARATION OF OIL-IN-WATER EMULSIONS OF DRUGS

[75] Inventors: Stanley S. Davis; Clive Washington, both of Nottingham, United Kingdom

[73] Assignee: The University of Nottingham, Nottingham, United Kingdom

[21] Appl. No.: 130,419

[22] PCT Filed: Aug. 21, 1990

[86] PCT No.: PCT/GB90/01309

§ 371 Date: Feb. 24, 1992

§ 102(e) Date: Feb. 24, 1992

[87] PCT Pub. No.: WO91/02517

PCT Pub. Date: Mar. 7, 1991

Related U.S. Application Data

[63] Continuation of Ser. No. 834,292, Feb. 24, 1992, abandoned.

[30] Foreign Application Priority Data

Aug. 23, 1989 [GB] United Kingdom ............ 8919172

[51] Int. Cl.[6] .............................................. A61K 9/107
[52] U.S. Cl. .................................. 424/400; 514/938; 514/31
[58] Field of Search .................. 424/400; 514/938, 31

[56] References Cited

U.S. PATENT DOCUMENTS

| | | | |
|---|---|---|---|
| 4,684,633 | 8/1987 | Imagawa et al. | 514/938 |
| 4,707,470 | 11/1987 | Kirsh et al. | 514/938 |
| 4,784,845 | 11/1988 | Desai et al. | 514/938 |
| 4,816,247 | 3/1989 | Desai et al. | 514/938 |
| 4,831,018 | 5/1989 | Kirsh et al. | 514/938 |
| 5,118,511 | 6/1992 | Horn et al. | 514/938 |

FOREIGN PATENT DOCUMENTS

| | | |
|---|---|---|
| 0009845 | 4/1980 | European Pat. Off. |
| 0202837 | 11/1986 | European Pat. Off. |
| 0296845 | 12/1988 | European Pat. Off. |
| 0317120 | 5/1989 | European Pat. Off. |

Primary Examiner—G. S. Kishore
Assistant Examiner—Amy Hulina
Attorney, Agent, or Firm—Nixon & Vanderhye

[57] ABSTRACT

A process for preparing an oil-in-water emulsion of a drug which is poorly soluble in water wherein the drug (e.g. amphotericin B) is dissolved in a solution of high or low pH prior to the formation of the drug emulsion. The solution of high pH is preferably a 0.5M solution of sodium hydroxide and/or potassium hydroxide and the solution of low pH is preferably a 0.5M solution of hydrochloric acid. The process comprises the steps of (a) dissolving the drug in a solution of high or low pH, (b) adding the resulting solution to a pre-formed emulsion, (c) adding to the emulsion an amount of an acid, base or buffer appropriate to neutralise at least substantially the product of step (b), and (d) where an acid or base is added in step (c), optionally adding sufficient buffer to adjust the pH of the product of step (c) to a desired value. A drug emulsion made by the process is also provided, in which the drug is primarily associated with the oil droplets.

17 Claims, 1 Drawing Sheet

PREPARATION OF OIL-IN-WATER EMULSIONS OF DRUGS

This is a continuation of application Ser. No. 07/834,292, filed Feb. 24, 1992, now abandoned.

The antibiotic amphotericin B is extremely beneficial in certain infectious conditions, particularly those caused by the fungal organism Candida. A common therapy is in the form of a product called Fungizone (Regd. T. M., Squibb) which consists of a solubilised formulation of amphotericin in the natural surfactant material sodium deoxycholate. This product is marketed by the Squibb Company. While helpful in combating Candida infections this product is not without its adverse reactions and side effects. It has been shown clearly that the Fungizone formulation can have a toxic effect particularly towards the kidney (see for example Reynolds et al (1963), Med. Clin. North American 47 1149-1154). The antibiotic properties of amphotericin are due to its binding to sterols in cell membranes and the subsequent formation of a membrane pore. The binding to ergosterol, the primary fungal sterol, is stronger than the binding to the mammalian sterol cholesterol. Hence the toxicity of amphotericin is only selective for fungal cells and not specific; this is the origin of the side effects in patients. Alternative strategies for administering amphotericin have been investigated and work conducted in Texas by Juliano, Lopez-Berenstein and others is particularly noteworthy (see for example Mehta et al (1984), Biochem. Biophys. Acta 770 230-234). These workers have employed a liposome formulation (phospholipid vesicle) in order to achieve benefit in terms of therapy. Others working along similar lines include the Squibb Company itself with the pro-liposome concept (see for example Payne et al (1987), J. Pharm, Pharmacol. 39 24-28). While the liposomal system might be beneficial clinically it is well known that liposomes are normally difficult to prepare reproducibly in bulk and can be unstable.

While it is possible to produce an amphotericin emulsion system by the simple admixture of a commercial fat emulsion product (Intralipid, (Regd. T. M., Kabi) with the commercial solubilised system of amphotericin (Fungizone) (see, for example, EP-A-202 837), this system is unstable in that it produces a precipitate of the drug after this admixture and also has poor stability if stored for more than a few hours. The amphotericin B apparently is not intercalated at the oil-water interface in the additive formulations.

EP-A-215 313 (American Cyanamid) discloses certain emulsions which break easily on administration to a patient. The drug is mixed with an oil phase before water is added to form an emulsion. Benzyl alcohol is used as a co-surfactant. The emulsions not only break quickly on administration but are not very stable in storage.

WO 82/01821 (Chinoin) discloses formulations which have the drug as a solid suspension dispersed throughout an emulsion. Again, the emulsions are not very stable and do not overcome the problem of toxicity of the drug; it is to be noted that all the prior formulations are for topical application.

EP-A-211258 (Abbott) discloses certain micro-emulsions, which are quite distinct from the emulsions of the present invention.

Our earlier application EP-A-296 845 describes the preparation of an oil-in water surfactant-stabilised drug emulsion in which the drug is present in the surfactant layer. This was found to reduce the problems of toxicity and stability encountered with prior formulations. However, the drug emulsion has to be sterilised, for example by heat treatment, and this may result in loss of around 10% of the drug. The resulting product is perfectly usable but it would clearly lead to cost savings if such losses could be avoided.

It is the intention of the present invention to provide a process for preparing a drug emulsion which reduces loss of activity of the drug during formulation.

The invention provides a process for preparing an oil-in-water emulsion of a drug which is poorly soluble in water wherein the drug is dissolved in a solution of high or low pH prior to the formation of the drug emulsion. A "solution of high pH" is a solution with a pH of at least 9, preferably at least pH 11. A "solution of low pH" is a solution with a pH of 5 or less, preferably pH3 or less.

Advantageously, the solution of high pH is a solution of sodium hydroxide, which is preferably between 0.1M and 5.0M, more preferably 0.5M. Potassium hydroxide may also be used, or a mixture of sodium and potassium hydroxide, to the same strength. A mixture of sodium and potassium may be advantageous to avoid disturbing the body's sodium/potassium ion balance. Any combination of sodium or potassium hydroxide may be used, and the proportions of these may be varied if this would be of clinical benefit to the individual patient.

Conveniently, the solution of low pH is hydrochloric acid, preferably at a concentration of between 0.1M and 5.0M, more preferably about 0.5M. Any clinically acceptable acid may be used providing that it induces a large enough change in solubility of the drug. This can be readily determined by a person skilled in the art.

Preferably, the process comprises the steps of (a) dissolving the drug in a solution of high or low pH, (b) adding the resulting solution to a pre-formed emulsion, (c) adding to the emulsion an amount of an acid, base or buffer appropriate to neutralise at Least substantially the product of step (b), and (d) when an acid or base is added in step (c), optionally adding sufficient buffer to adjust the pH of the product of step (c) to a desired value. After addition of acid or base in step (c), a small sample of the emulsion may be withdrawn and tested by any suitable means to see if the pH is at the desired value. If it is not, buffer can be added. It will usually be desirable to have a neutral emulsion, i.e. about pH 7.4.

Any acid, base or buffer which is clinically acceptable may be used in step (c). Desirably, the acid is hydrochloric acid, acetic acid or glucuronic acid, the base is sodium hydroxide or potassium hydroxide and the buffer is an amino acid buffer or a phosphate buffer.

Any commercially available, parenterally acceptable emulsion may be used, for example Intralipid (Regd. T. M.), Ivelip (Regd. T. M.), Lipofundin (Regd. T. M.), Elolipid (Regd. T. M.), Endolipid and the MCT/LCT emulsion available from Braun. A typical emulsion may contain 3% to 30% soya, safflower or coconut oil (although coconut oil would not be used i.v.) and 0.2% to 5% of a parenterally acceptable emulsifier such as egg or soya lecithins, which may have been fractionated or hydrogenated to provide specific properties. The emulsion may also contain a tonicity adjusting agent such as glycerol, and amino-acids and glucose. The formulation and properties of such systems are familiar to those skilled in the art.

The procedure may also be used to add a hydrophobic drug to any parenterally acceptable dispersion for which the drug has sufficient affinity, such as liposomes, microparticulates or microemulsions.

A salt will be formed by the acid and alkali in the emulsion. In the case of sodium hydroxide and hydrochloric acid, sodium chloride will be formed; to avoid destabilisation of the emulsion, the final concentration of the salt should be less than 50 mM, preferably less than 10 mM. The presence of this salt will contribute to the tonicity of the drug emulsion. It may therefore be possible to use a pre-formed emulsion which contains little or no tonicity agent.

Desirably, the solution resulting from step (a), the pre-formed emulsion, the acid and the buffer, if used, are sterile at the time of use in the process described above. This can be achieved by carrying out the additions of solutions in steps (b), (c) and (d) by injection through a sterility filter. Such filters are well known to those skilled in the art. The pore size of the filter should be sufficiently small to remove all microorganisms, thus rendering them sterile. A 0.2 μm pore would be suitable. No other sterilisation step, such as heat treatment, is required, although pyrogen-free materials should be used to avoid toxic shock. This has been found to reduce the problem of loss of drug activity usually encountered by such sterilisation procedures.

A second aspect of the invention provides an emulsion formed by the process described above in which the drug is primarily associated with the oil droplets. By "primarily associated with", we mean that at least 50% of the drug is associated with the oil droplets, preferably 60%, 70%, 80%, 90% or 99%. Most preferably, substantially all of the drug is associated with the oil droplets. The oil droplets may be separated from the emulsion by centrifugation and the drug shown to be in the oil layer.

The drug used in the emulsion is preferably one which is poorly soluble in water. By poorly soluble, we mean one which is insufficiently soluble for therapeutic levels to be achieved by the administration of a convenient volume of a solution of the drug, In terms of an infusion of a formulation containing the drug, it would generally be the case that one would wish to administer less than 100 ml of the formulation per hour, preferably less than 50 ml/hour, more preferably less than 30 or 10 ml/hour. In essence, the formulations of the invention are particularly suitable for drugs which would be categorised in pharmacopoeias as "practically insoluble" in water. However, the drug must be soluble at either low or high pH.

The person skilled in the art will readily be able to determine by routine and non-inventive experiments whether a drug is suitable.

The drug may be a general anaesthetic, local anaesthetic, hypnotic, sedative, autacoid or autacoid antagonist (for example a prostaglandin), antibiotic or antimicrobial, antineoplastic (especially cytotoxic drugs such as methotrexate) or immunosuppressant. A particularly preferred group of drugs is the polyene antibiotics including tetraenes such as nystatin, pentaenes such as aliomycin, methylpentaenes such as filipin, carbonylpentaenes such as mycoticin, hexaenes such as cryptocidine, carbonylhexaenes such as dermostatin, and heptaenes such as amphotericin B. Such antibiotics are commercially available or can be conventionally prepared by techniques known to one of skill in the art. Preferably, the said drug is amphotericin B, nystatin or filipin, most preferably amphotericin B. For these drugs, strong alkali is used in the first step of the process. Strong acid may be used to dissolve basic drugs such as amodiaquine, bupivacaine, chlorcyclizine, chlorpromazine, dextromethorphan, diphenhydramine, ethopropazine, fenfluramine, fluopromazine, fluphenazine, imipramine, meclozine, nortryptyline, phenazocine, phencyclidine, promazine, promethazine, trifluoroperazine, triflupromazine or verapamil, or other active compounds which form soluble acid salts, especially hydrochlorides.

The level of drug may be chosen by one skilled in the art to suit the dosage regimen and so on but may typically be up to 5 mg/ml, preferably about 1 or 2 mg/ml, in the case of amphotericin B.

Emulsions in accordance with the invention can be administered topically, orally, rectally or by "aerosolisation" into the lungs, but will usually be administered parenterally, for example by continuous intravenous infusion or by injection, which may be intravenous, subcutaneous or intramuscular. Sustained release preparations such as subcutaneous depots may be used. The daily dose will be determined by the skilled person, with reference to the patient, the disease and the drug, but might typically be 0.10 mg/kg/day to 10 mg/kg/day, total body weight.

In the case of the polyene antifungal drugs such as amphotericin B, the formulations of the invention are useful in the treatment of humans or animals suffering from a variety of fungal infections, for example caused by any species of Candida (especially *C. albicans* and *C. tropicalis*), *Torulopsis glabrata* and *Aspergillus* spp. These infections are especially common, and serious, in immunocompromised patients, such as those treated with immunosuppressant drugs or those suffering from Acquired Immunodeficiency Syndrome (AIDS; acute HIV infection).

The emulsion of the present invention may be made up by a manufacturer, or by a pharmacist immediately prior to use. The latter situation may be advantageous for drugs which destabilize the emulsion. The drug emulsion would then have to be made immediately prior to use. An alternative embodiment of the invention therefore provides a kit comprising (a) a known amount of drug (b) a known amount of solution of high or low pH, and (c) an amount of acid, base or buffer appropriate to at least substantially neutralise the solution of high or low pH. Conveniently, the kit additionally comprises (i) a preformed emulsion, and (ii) at least one sterility filter.

The drug emulsion may be used as part of a total parenteral nutrition (TPN) system. In this case, the drug emulsion is formulated and is then compounded with the TPN constituents, (sugars, amino acids, etc). This avoids destabilization of the TPN mixture. For some drugs, where the volume of solution used in step (a) of the formulation process is small, it may be possible to omit the neutralisation step (c) as the TPN mixture may itself have sufficient buffering capacity to neutralise the emulsion.

The process of the present invention is simple to carry out and has been found to produce an emulsion which has increased particle size stability. The process also avoids the use of a co-solvent for the drug, such as methanol. The presence of such a solvent in an emulsion for parenteral administration is regarded by many as unacceptable, even when present only in traces.

Figure 2:
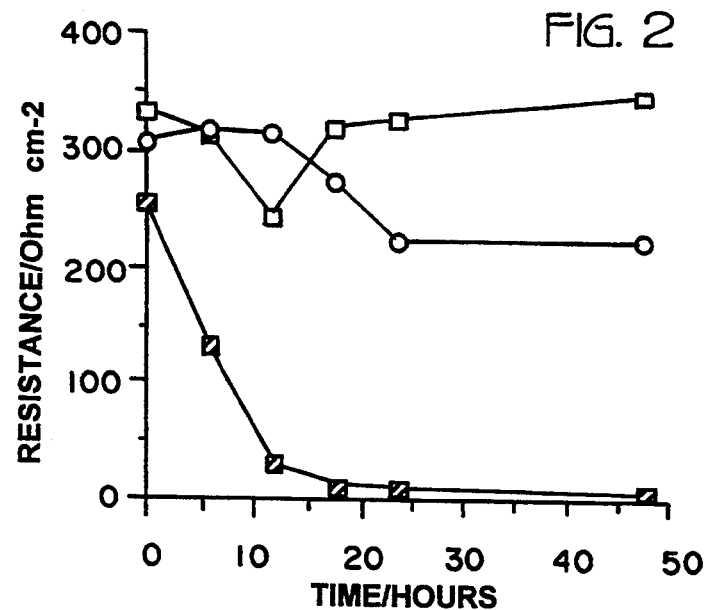
Figure 3:
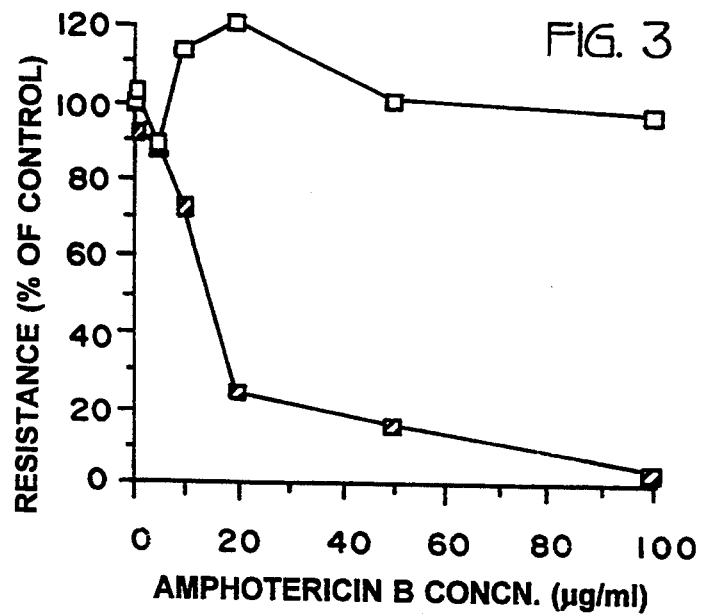

A preferred embodiment will now be described by way of example and with reference to the accompanying drawings in which FIG. 1 shows a conventional bacterial filter and FIGS. 2 and 3 show toxicity data.

EXAMPLE 1

Preparation of an Amphotericin B emulsion 100 mg Amphotericin B was dissolved in 2 ml of 0.5M sodium hydroxide with the aid of sonication. The solution was then drawn into a syringe and injected through a 0.2 μm filter as shown in FIG. 1 into a 100 ml bottle of Intralipid 20%. 2 ml of water for injection was then drawn into the syringe and injected into the emulsion through the same filter. 2 ml of 0.5M hydrochloric acid was then injected into the emulsion through the filter and followed by 2 ml of water for injection. 2 ml of 0.1M phosphate buffer at pH 7 was then added. The whole bottle was thoroughly mixed by shaking.

The filter of FIG. 1 comprises a sealed housing 1 having respective top (entry) and bottom (exit) ports 2,3 for liquids, the housing 1 being divided into two compartments 4,5 by a 2 μm pore membrane filter 6 supported on a filter support 7. Liquid to be sterilised enters the first compartment 4, passes through the filter 6 into the second compartment 5 and, thus sterilised, leaves through the exit port 3.

EXAMPLE 2

Stability of the emulsion

The emulsion prepared by the above method showed no detectable increase in droplet size over a 50 day period. (Malvern Mastersizer; D (v. 0.9)=0.72 μm at t=0, 0.68 μm at t=50 day).

EXAMPLE 3

Stability of the Amphotericin B

The emulsion was dispersed in dimethyl sulphoxide and the absorbance of amphotericin was measured at 514 nm.

The amphotericin B concentration decreased from 0.46 mg/ml at t=0 to 0.43 mg/ml after 50 days.

EXAMPLE 4

Toxicity of Amphotericin B emulsion to canine kidney cells in monolayer culture

The toxicity of a formulation prepared as in Example 1 above to canine kidney cells was measured in monolayer culture for extended periods. The cell line (MDCK NBL-2) was established in a modified MEM medium and grown as a confluent monolayer on Millicell HA filters. The integrity of the monolayer was measured via its resistance. The cell monolayers were transferred to calcium- and magnesium-free Hanks' balanced salt solution (HBSS) to avoid emulsion flocculation, concentrations of amphotericin B formulations up to 100 μg/ml were added, and the resistance measured over a period of 48 hours. Control experiments were performed with an amphotericin-free emulsion (Intralipid 20% and a commercial amphotericin formulation (Fungizone, Squibb). A typical plot of resistance vs. time is shown in FIG. 2 (amphotericin concentration 10 μg ml$^{-1}$). Fungizone is represented by solid squares, Amphotericin emulsion by open squares and the Intralipid control by open circles. The loss of confluence on addition of Fungizone is evident within 6 hours, and is demonstrated by a severe drop in monolayer resistance. Only a small decrease is observed using either the Intralipid control or the amphotericin emulsion formulation, and we believe this to be due to minor changes in cell viability after changing to low-salt HBSS medium. The dose-response curve, calculated as a percentage of the control resistance after 6 hours, is shown in FIG. 3. Fungizone is represented by solid squares and the Amphotericin emulsion by open squares. The low toxicity of the emulsion formulation is maintained up to an amphotericin concentration of 100 μg ml$^{-1}$.

The results clearly demonstrate the low toxicity to kidney cells of the amphotericin B emulsion formulation.

EXAMPLE 5

Preparation of chlorpromazine emulsion

To make approximately 100 ml of an emulsion containing 2 mg/ml chlorpromazine.

Chlorpromazine (200 mg) was dissolved in hydrochloric acid (0.5M; 2 ml) and injected through a 0.2 μm filter into a 100 ml bottle of Intralipid 20%. The filter was rinsed through with 2×1 ml portions of water for injection. Sodium hydroxide (0.5M, 2 ml) was then injected through the same filter, followed by phosphate buffer (0.5M, pH 7.0, 1 ml). The bottle was swirled continuously during all additions.

We claim:

1. A process for preparing an oil-in-water emulsion of a drug which is poorly soluble in water, said process comprising the steps of:
   (a) dissolving the drug in a solution of high pH having a pH of at least 9 or low pH having a pH of 5 or less;
   (b) adding the resultant solution to a pre-formed emulsion;
   (c) adding to the emulsion an amount of an acid, base or buffer appropriate to neutralize at least substantially the product of step (b).

2. A process according to claim 1, wherein said solution of high pH is selected from the group consisting of a solution of sodium hydroxide and potassium hydroxide between 0.1M and 5.0M.

3. A process according to claim 2, wherein the hydroxide solution is substantially 0.5M.

4. A process according to claim 1, where the drug is a polyene antibiotic.

5. A process according to claim 4, wherein the drug is amphotericin B.

6. A process according to claim 1, wherein the solution is a solution of low pH and is hydrochloric acid between 0.1M and 5.0M.

7. A process according to claim 6, wherein the hydrochloric acid is substantially 0.5M.

8. A process according to claim 1, wherein, when an acid or base is added in step (c), sufficient buffer is added to adjust the pH of the product of step (c) to a desired value.

9. A process according to claim 8, wherein the acid used in step (c) is selected from the group consisting of hydrochloric acid, acetic acid and glucuronic acid, the base used in step (c) is selected from the group consisting of sodium hydroxide and potassium hydroxide and the buffer used in step (c) is selected from the group consisting of an amino acid buffer and a phosphate buffer.

10. A process according to claim 8, wherein the final concentration of salt formed in the emulsion is less than 50 mM.

11. A process according to claim 10, wherein the final concentration of salt formed in the emulsion is less than 10 mM.

12. A process according to claim 1, wherein the solution resulting from the step (a), the preformed emulsion, and the acid, base or buffer of step (c) are sterile at the time of use in said process.

13. A process according to claim 8, wherein the solution resulting from the step (a), the preformed emulsion, and the acid or base of step (c) and the buffer added to adjust the pH of the product of step (c) to a desired value are sterile at the time of use in said process.

14. An emulsion made by the process according to claim 1, wherein the drug is poorly soluble in water and is primarily associated with the oil droplets.

15. A kit for making an oil-in-water emulsion of a drug which is poorly soluble in water, comprising:

(a) known amount of said drug which is poorly soluble in water;
(b) a known amount of a solution of high pH having a pH of at least 9 or low pH having a pH of 5 or less; and
(c) an amount of acid, base or buffer appropriate to neutralize at least substantially the solution of high or low pH.

16. A kit according to claim 15, additionally comprising (i) a pre-formed emulsion and (ii) at least one sterility filter.

17. A method of treating or preventing disease in a human or other animal, said method comprising the step of administering to the human or animal an effective non-toxic amount of an emulsion of a drug which is poorly soluble in water made according to the process of claim 1.

* * * * *